United States Patent [19]

Rahim et al.

[11] Patent Number: 4,863,906

[45] Date of Patent: Sep. 5, 1989

[54] 2'-DEOXY-5-ETHYNYLURIDINE-3',5'-DIESTENS FOR TREATMENT OF VZV AND CMV INFECTIONS

[75] Inventors: Saad G. Rahim; John W. T. Selway, both of Beckenham, England

[73] Assignee: Burroughs Wellcome Co., Research Triangle Park, N.C.

[21] Appl. No.: 883,913

[22] Filed: Jul. 10, 1986

[30] Foreign Application Priority Data

Jul. 10, 1985 [GB] United Kingdom ............... 8517402

[51] Int. Cl.$^4$ ................ A61K 31/505; C07H 19/06
[52] U.S. Cl. ...................................... 514/50; 536/23
[58] Field of Search ...................... 514/50, 49; 536/23

[56] References Cited

U.S. PATENT DOCUMENTS

| | | | |
|---|---|---|---|
| 4,247,544 | 1/1981 | Bergstrom et al. | 514/50 |
| 4,424,211 | 1/1984 | Jones et al. | 514/50 |
| 4,544,740 | 10/1985 | Szaboles née Borbas et al. | 536/23 |
| 4,594,339 | 6/1986 | Lopez et al. | 514/49 |

FOREIGN PATENT DOCUMENTS

| | | |
|---|---|---|
| 1601020 | 10/1981 | European Pat. Off. . |
| 0282668 | 6/1983 | European Pat. Off. . |
| 0175004 | 3/1986 | European Pat. Off. . |

OTHER PUBLICATIONS

Journal of the Chemical Society, Perkin Transaction I, 1978, pp. 1263–1267.
Journal of the Chemical Society, Perkin Transaction I, 1981, pp. 1665–1670.
Tetrahedron, vol. 36, 1980, pp. 155–158.
Chemical Abstracts, vol. 91, 1979, pp. 26 and 27, abstract No. 133836c and Proc. Natl. Acad. Sci., U.S.A., 1979, 76(6), 2947–51.
Journal of Organic Chemistry, vol. 48, No. 11, 1983, pp. 1854–1862, Am. Chem. Soc. US.
DeClercq, Methods and Findings in Experimental Clinical Pharmacology, vol. 2(5), pp. 253–267, 1980.
Barr et al., J. Chem. Soc., Perkin I, pp. 1263–1267, 1978.
Perman et al., Tett. Lett., pp. 2427–2430, 1976.
Robins et al., J. Org. Chem., vol. 48, pp. 1854–1862, 1983.
Robins et al., Can. J. of Chem., vol. 60, pp. 554–557, 1982.
Millen et al., J. of Virology, vol. 23, pp. 679–684, 1977.
Streissle et al., Advances in Virus Research, vol. 30, pp. 83–138, 1985, Academic Press.
Walker et al., Nucleic Acids Research Symposium Series, No. 16, pp. 291–294, 1985.
De Clercq et al., J. of Infections Diseases, vol. 141, pp. 563–574, 1980.
De Clercq et al., Proc. Nat. Acad. Sci., U.S.A., vol. 76, pp. 2947–2951, 1979.
DeClercq et al., Molecular Pharmacology, vol. 21, pp. 217–223, 1982.
Saran et al., Quantum Chemistry, Symposium, No. 9, pp. 247–257, 1982.
Perlman et al., J. Med. Chem., vol. 28, pp. 741–748, 1985.
De Clercq et al., Pharmaceutical Therspies, vol. 26, pp. 1–44, 1984.
Shealy et al., J. Med. Chem., 29, 79–84, 1986.
DeClercq et al., Molecular Pharmacology, vol. 19, pp. 321–330, 1981.
DeClercq et al., J. Med. Chem., vol. 26, pp. 661–666, 1983.
Perman et al., Tett. Lett., 1976, pp. 2427–2430.

Primary Examiner—Ronald W. Griffin
Assistant Examiner—L. Eric Crane
Attorney, Agent, or Firm—Donald Brown

[57] ABSTRACT

The present invention relates to the use of 2'-deoxy-5-ethynyluridine and its pharmaceutically acceptable derivatives in the treatment and prophylaxis of varicella zoster virus and cytomegalovirus infections. Also provided are pharmaceutical formulations and processes for the preparation of the compounds according to the invention.

8 Claims, No Drawings

2'-DEOXY-5-ETHYNYLURIDINE-3',5'-DIESTENS FOR TREATMENT OF VZV AND CMV INFECTIONS

The present invention relates to the use of a pyrimidine, or physiologically acceptable salt thereof, in the treatment of certain DNA virus diseases.

Cytomegalovirus (CMV) forms a class of DNA viruses belonging to the family Herpesviridae. In common with the herpes viruses, infection with CMV leads to a lifelong association of virus and host and, following a primary infection, virus may be shed for a number of years. Infection may be acquired in infancy or early adulthood and, in the foetus, intra-uterine infection is probably the commonest form of infection, but up to 90% of congenital infections are asymptomatic at birth. Primary infection of the mother during pregnancy is generally considered to pose the greatest risk to the unborn child, whereas in reactivation the foetal infections are usually clinically silent. Clinical effects range from death and gross disease (microcephaly, hepatosplenomegaly, jaundice, mental retardation) through failure to thrive, susceptibility to chest and ear infections to a lack of any obvious ill effect. In young adults infection may well go unnoticed or manifest as a glandular fever like disease resulting from close physical contact.

In addition to primary infections, equally serious infections may occur due to reactivation of the dormant virus in immuno-compromised patients. Such infections result in increased morbidity and fatality from retinitis, pneumonitis and gastrointestinal disease. Such patients may be immuno-compromised either as a result of therapy or of disease. Of the former, the worst infections are seen in bone-marrow transplant and kidney transplant patients. Patients immuno-compromised through disease are now seen in increasing numbers with the advent of AIDS, a condition which naturally destroys the immune system, leaving the victim vulnerable to infections which would not otherwise be dangerous. CMV infection in AIDS patients is a predominant cause of morbidity as, in 80% of the adult population, it is present in a latent form and can be re-activated in immuno-compromised patents.

In "Viral Infections of Humans" (2nd Ed., Ed., Evans, A. S. (1982) Plenum Publishing Corporation, New York), Chapter 8 describes in some detail the aetiology of CMV infections.

To date there is no recognised therapy for CMV disease. CMV immunoglobulin has been used with some success prophylactically and is now marketed. In patients who are only slightly immunosuppressed, for example renal transplant patients, prophylaxis or prompt therapy with human interferon or acyclovir has resulted in a clinical response. Varicella zoster virus (VZV), another virus of the herpes family, causes chicken pox, pneumonitis, encephalitis, intravascular coagulopathy, disseminated zoster, hepatitis, shingles and keratitis. As with CMV infections, the therapeutic treatment of VZV infections has proved difficult.

Attention has focussed on nucleoside analogues for the treatment of viral infections. One compound, originally of interest as a useful intermediate, is 2'-deoxy-5-ethynyluridine, the synthesis of which is disclosed by Barr et al. (J. Chem. Soc. Perkin Trans. I (1978), 1263). Its antiviral screening is described for example by Walker et al. (Nuc. Ac. Res., Special Pub. No. 4, 1978) and in UK patent specification No. 1 601 020. Activity was assayed against vaccinia and herpes simplex viruses, but showed only moderate activity.

It has now surprisingly been found that 2'-deoxy-5-ethynyluridine has very potent activity against certain DNA viruses other than those referred to above.

Thus in a first aspect of the present invention, there is provided a compound of formula (I):

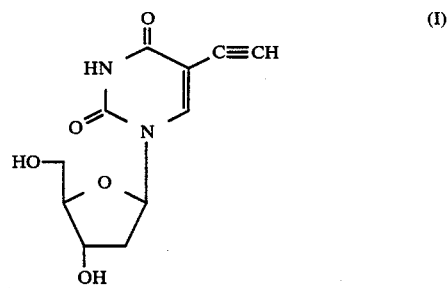

(2'-deoxy-5-ethynyluridine), or a pharmaceutically acceptable derivative thereof for use in the treatment or prophylaxis of human viral infections caused by CMV or VZV.

Thus, in a further, preferred aspect of the present invention, there is provided the use of a compound according to the invention in the manufacture of a medicament for the treatment or prophylaxis of human viral infections caused by CMV or VZV. Examples of the clinical caused by CMV and VZV infections which may be treated in accordance with the invention include those referred to above.

The present invention further provides a method for the treatment or prophylaxis of CMV or VZV infections in a human subject which comprises administering to the said human subject an effective amount of a compound according to the invention.

The method hereinbefore described includes inhibiting the replication of CMV or VZV viruses in host cells of a mammal which comprises applying an effective virus replication inhibiting amount of the compound of formula (I), or a pharmaceutically acceptable derivative thereof, to the infected cells.

By "a pharmaceutically acceptable derivative" is meant any pharmaceutically acceptable salt, ester, or salt of such ester, or any other compound which, upon administration to a human subject, is capable of providing (directly or indirectly) 2'-deoxy-5-ethynyluridine or an antivirally active metabolite or residue thereof.

Preferred esters of the compound of formula (I) include carboxylic acid esters in which the non-carbonyl moiety of the ester grouping is selected from straight or branched chain alkyl, alkoxyalkyl (e.g. methoxymethyl), aralkyl (e.g. benzyl), aryloxyalkyl (e.g. phenoxymethyl), aryl (e.g. phenyl optionally substituted by halogen, $C_{1-4}$ alkyl or $C_{1-4}$ alkoxy); sulphonate esters such as alkyl- or aralkylsulphonyl (e.g. methanesulphonyl); and mono-, di- or tri-phosphate esters. With regard to the above-described esters, unless otherwise specified, any alkyl moieties present in such esters advantageously contain 1 to 18 carbon atoms, particularly 1 to 4 carbon atoms. Any aryl moiety present in such esters advantageously comprises a phenyl group. Any reference to any of the above compounds also includes a reference to a pharmaceutically acceptable salt thereof.

Salts of the compound of formula (I) which may be conveniently used in therapy include physiologically acceptable base salts, eg derived from an appropriate base, such as alkali metal (e.g. sodium), alkaline earth metal (e.g. magnesium) salts, ammonium and $NX_4^+$ (wherein X is $C_{1-4}$ alkyl).

The present invention thus further provides the novel pharmaceutically acceptable derivatives of the compound of formula (I) e.g. as described above. Particularly preferred examples of such novel derivatives include the pharmaceutically acceptable esters, eg the mono- and di-pivalate esters, and also the pharmaceutically acceptable salts, eg the sodium salt of the compound of formula (I).

The compound of formula (I) and pharmaceutically acceptable derivatives thereof (hereafter collectively referred to as the active ingredients) may be administered by any route appropriate to the condition to be treated, suitable routes including oral, rectal, nasal, topical (including buccal and sublingual), vaginal and parenteral (including subcutaneous, intramuscular, intravenous, intradermal, intrathecal and epidural). It will be appreciated that the preferred route may vary with, for example, the condition of the recipient.

For each of the above-indicated utilities and indications the amount required of an active ingredient (as above defined) will depend upon a number of factors including the severity of the condition to be treated and the identity of the recipient and will ultimately be at the discretion of the attendant physician. In general, however, for each of these utilities and indications, a suitable, effective dose will be in the range 0.1 to 250 mg per kilogram body weight of recipient per day, preferably in the range 1 to 100 mg per kilogram body weight per day and most preferably in the range 5 to 20 mg per kilogram body weight per day; an optimum dose is about 15 mg per kilogram body weight per day (unless otherwise indicated all weights of active ingredient are calculated as the parent compound of formula (I); for salts and esters thereof the figures would be increased proportionately.) The desired dose is preferably presented as two, three, four or more sub-doses administered at appropriate intervals throughout the day. These sub-doses may be administered in unit dosage forms, for example, containing 10 to 1000 mg, preferably 20 to 500 mg and most preferably 100 to 400 mg of active ingredient per unit dosage form.

While it is possible for the active ingredients to be administered alone it is preferable to present them as pharmaceutical formulations. The formulations of the present invention comprise at least one active ingredient, as above defined, together with one or more acceptable carriers thereof and optionally other therapeutic ingredients. The carrier(s) must be "acceptable" in the sense of being compatible with the other ingredients of the formulation and not deleterious to the recipients thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide the desired release profile.

For infections of the eye or other external tissues, e.g., mouth and skin, the formulations are preferably applied as a topical ointment or cream containing the active ingredient in an amount of, for example, 0.075 to 20% w/w, preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active ingredient through the skin or other affected areas. Example of such dermal penetration enhancers include dimethylsulphoxide and related analogues.

The oil phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl mono-stearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

The administered ingredients may also be used in therapy in conjunction with other medicaments such as 9-[[2-hydroxy-1-(hydroxymethyl)ethoxy]methyl]guanine, 9-(2-hydroxyethoxymethyl)guanine (acyclovir), 2-amino-9-(2-hydroxyethoxymethyl)purine, interferon, e.g., α-interferon, interleukin II, and phosphonoformate (Foscarnet) or in conjunction with other immune modulating therapy including bone marrow or lymphocyte transplants or medications such as levamisol or thymosin which serve to increase lymphocyte numbers and/or function as is appropriate.

The compound of formula (I) and its pharmaceutically acceptable derivatives may be prepared by any of the methods known in the art for the preparation of the same or similar compounds e.g. see UK patent specification No. 1 601 020, or Robins, M. J. and Barr, P. J., J. Org. Chem. (1983) 48, 1854–1862.

The present invention also provides a process for the preparation of a compound of formula (I), or a pharmaceutically acceptable derivative thereof, comprising either:

A. reducing a compound of formula

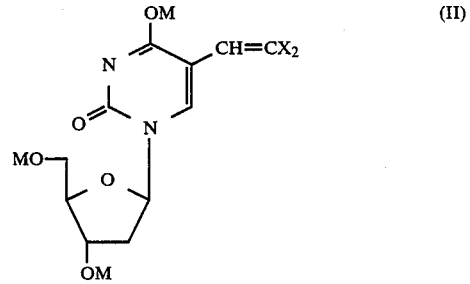

wherein X represents halogen and M is a protecting group; or

B. condensing a compound of formula

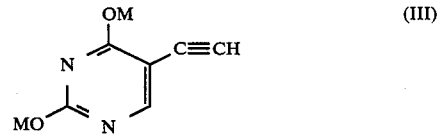

wherein M is defined above, with a compound of formula

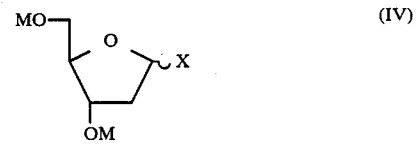

wherein X and M are as defined above; or

C. reacting a compound of formula

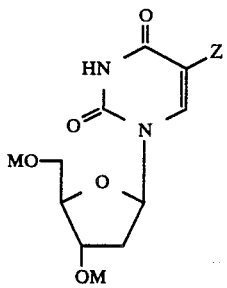

(V)

wherein M is as defined above and Z is a leaving group, with a compound capable of providing the necessary ethynyl grouping; and, optionally thereafter or simultaneously therewith, performing either or both of the following:

(i) removing any remaining protecting groups;
(ii) where the resulting compound is a compound of formula (I), converting it into a pharmaceutically acceptable derivative thereof or, where the resulting compound is a pharmaceutically acceptable derivative, converting it into a different pharmaceutically acceptable derivative or a compound of formula (I).

With regard to process (A), the compound of formula (II) is conveniently protected with conventional blocking groups such as acyl groups, eg alkanoyl or aroyl groups such as p-toluoyl, or trialkylsilyl groups such as TMS. The reduction may be effected, for example, by treatment with an organometallic reagent such as phenyllithium in an ethereal solvent, such as THF, preferably below 0° C., conveniently −50°–0° C. The protecting group can subsequently be removed by acid hydrolysis. This process is described by Perman et al. (Tetrahedron Letters (1976), 28, 2427).

Regarding process (B), suitable blocking groups may be selected from any known in the art for example those referred to above in relation to process (A). The halogen of the sugar residue (formula (IV)) is conveniently chlorine and the reaction carried out in the presence of a Lewis acid catalyst, for example stannic chloride, in an appropriate solvent, such as 1,2-dichloroethane. The parent compound can then be obtained, following anomeric separation, by treatment with alcoholic base, such as sodium methoxide in methanol. This process is also described by Barr, et al., in J. Chem. Soc., Perkin 1(1978), 1263 et seq.

Regarding process (C), this is exemplified by Robins, M.J., and Barr, P.J., in J. Org. Chem. (1983), 48,1854 et seq. A 5-halogenated nucleoside such as 2'-deoxy-5-iodouridine in the 3',5'-diacylated, or otherwise suitably protected form, for example with the protecting groups referred to above, can be subjected to a catalysed coupling reaction, for example with a palladium catalyst, with a protected acetylene, such as trimethylsilylacetylene, in the presence of an organic base, such as triethylamine, and another metal catalyst, for example a copper (I) salt, at an elevated temperature such as 50° C. to give the protected acetylenic nucleoside. A preferred palladium catalyst is bis(triphenylphosphine)-palladium dichloride and a preferred copper catalyst is cuprous iodide. The parent compound can readily be obtained by treatment with alcoholic base, such as sodium methoxide in methanol.

The compound of formula (II) in process (A) can be prepared for example by condensation of a compound of formula

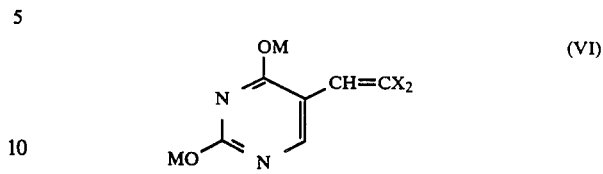

(VI)

wherein M and X are as defined above, with a compound of formula (IV), conveniently in the presence of a Lewis acid catalyst such as stannic chloride in, for example, 1,2-dichloroethane at a low temperature, such as 0°–5° C., to give the protected nucleoside as an anomeric mixture which can be separated. The compound of formula (VI) is conveniently obtained by a Wittig reaction between a compound of formula

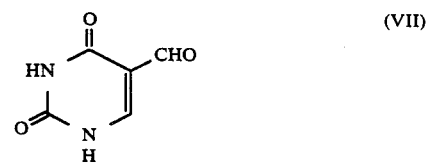

(VII)

and (dihalomethylene)triphenylphosphorane, conveniently in an appropriate organic solvent mixture such as DMF and methylene chloride at room temperature.

In process (B), the compound of formula (III) may be prepared, for example, by halogenating 5-acetyluracil with a suitable halogenating agent, such as phosphoryl chloride, in the presence of base to yield a compound of formula (VIII)

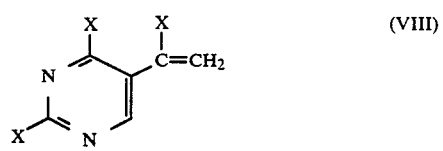

(VIII)

wherein X is halogen. The compound of formula (VIII) may then be further reduced and then protected, to yield the compound of formula (III)

Esters according to the invention may be prepared in conventional manner e.g. by treatment of the parent compound of formula (I) with an appropriate esterifying or transesterifying agent, for example, by treatment of 2'-deoxy-5-ethynyluridine with an appropriate acid halide (e.g. chloride) or anhydride in the presence of base, conveniently pyridine, which may also be used as the solvent.

Salts according to the invention may also be prepared in conventional manner for example with an appropriate base to form the corresponding base salt. Other derivatives according to the invention can also be prepared in conventional manner.

The following Examples illustrate the present invention.

EXAMPLE 1

A. 2'-Deoxy-3',5'-di-O-p-toluoyl-5-(2-trimethylsilylethynyl)uridine

To a stirred suspension of 2'-deoxy-3',5'-di-O-p-toluoyl-5-iodouridine (7 g, 11.85 mmoles) in dry triethylamine (300 ml) under nitrogen was added trimethylsilylacetylene (23.7 mmoles), bis(triphenylphosphine)palladium dichloride (0.17 g) and cuprous iodide (0.17 g) and the whole was stirred at 50° C. for 6 hours. The solvent was then removed under reduced pressure and the residue dissolved in chloroform (250 ml), washed with 5% disodium EDTA/water (200 ml, twice) and water (300 ml) and dried. The solvent was evaporated and the residue dissolved in the minimum of hot chloroform to which was added methanol (5 volumes). The solution was cooled for 24 hours and the mixture filtered and dried to give the title compound as a grey solid (5.87 g, 88% yield). NMR analysis and tlc (5%, 1:9, MeOH/CH$_2$Cl$_2$) showed it to be pure.

B. 2'-Deoxy-5-ethynyluridine

The title compound of (A) (5.87 g, 0.01 moles) was added to a solution of sodium (0.276 g, 0.012 moles) in dry methanol (100 ml) and stirred at room temperature for 2 days. The solution was then neutralised with Amberlite H$^+$ resin, the mixture filtered, the resin washed with methanol and the filtrate and washing evaporated. The crude solid was recrystallised from methanol with decolourising charcoal to give a first crop of the title compound (1.38 g) as pale, brown crystals. Concentration of the mother liquor afforded a second crop which was also recrystallised from methanol (0.65 g). The total yield was thus 2.03 g (80.5%). M.p. 175° C. Pure by NMR and tlc (5%, 1:9, MeOH/CH$_2$Cl$_2$).

Microanalysis Calc: C, 52.40%; H, 4.76%; N, 11.11% for C$_{11}$H$_{12}$N$_2$O$_5$. Fnd: C, 52.00%; H, 4.81%; N, 11.02%.

EXAMPLE 2

2'-Deoxy-5-ethynyl-5'-O-pivaloyluridine and 2'-Deoxy-5-ethynyl-3',5'-di-O-pivaloyl uridine Pivaloyl chloride (0.3 ml, 2.56 mmoles) was added to a cooled, stirred solution of 2'-deoxy-5-ethynyluridine (0.5 g, 1.98 mmols) in dry pyridine (5 ml) and stirring was maintained at room temperature for 3 hours. TLC in CH$_2$Cl$_2$/MeOH (19:1) revealed complete reaction. The mixture was poured onto ice/water, methylene chloride added, the organic layer separated and washed with water, dried with sodium sulphate and evaporated to dryness. The residue was chromatographed on silica gel eluted with CH$_2$Cl$_2$/MeOH. The first product was triturated with hexane to give 2'-deoxy-3',5'-di-O-pivaloyl-5-ethynyluridine. M.p. 151° C.

NMR: δCDCl$_3$ 7.8(1H, s, H-6), 6.6–6.0(3H, m, H-1', NH, OH-3'), 4.7–4.1 (4H, m, H-3', H-4' and H-5'), 3.22 (1H, s, acetylenic H), 2.6 (1H, m H-2'), 2.3 (1H, m, H-2'), 1.3 ppm (9H, s, tBu-H)

Calc. C. 60.03: H, 6.66-N. 6.66%. Fnd. C. 59.53-H. 6.58-N. 6.45.

The second product eluted was triturated with hexane to give 2'-deoxy-5-ethynyl-5'-O-pivaloyl-uridine. M.p. 64°–66° C.

NMR: δCDCl$_3$ 8.65 (1H, bs, NH), 7.8 (1H, s, H-6), 6.2 (1H, dd, H-1'), 5.2 (1H, m, H-3'), 4.5–4.2 (3H, m, H-4' and H-5'), 3.18 (1H, s, acetylenic H), 2.6 (1H, m, H-2'), 2.1 (1H, m, H-2'), 1.2 ppm (18H, d, tBu-H).

Calc. C. 57.17-H. 5.93-N. 8.33%. Fnd. C. 57.09-H. 6.01-N. 8.03%.

EXAMPLE 3

2'-Deoxy-3'-5'-di-O-acetyl-5-ethynyluridine

To a stirred solution of 2'-deoxy-5-ethynyluridine (0.5 g, 2 mmoles) in dry pryidine (8 ml) at 0° C. was added acetic anhydride (0.6 g, 6 mmols) and stirring maintained at room temperature overnight. The solvent was evaporated in vacuo and coevaporated with ethanol. The residual mass was triturated with ethanol, filtered and recrystallized from ethanol to give the title compound (0.61 g, 91%).

Mp 138°–140° C.

NMR: δCDCl$_3$ 8.4 (1H, s, NH), 7.9 (1H, s, H-6), 6.3 (1H, t, H-1'), 5.8 (1H, m, H-3'), 4.35 (3H, m, H-4' and H-5'), 3.2 (1H, s, acetylenic H), 2.35 (2H, m, H-2'), 2.12 ppm (6H, d, OCH$_3$).

CHN Calc: C, 53.57; H, 4.76; N, 8.33%. Fnd. C, 53.66; H, 4.72; N, 7.95%.

EXAMPLE 4

2'-Deoxy-3'-5'-di-O-methanesulphonyl-5-ethynyluridine

To a stirred solution of 2'-deoxy-5-ethynyluridine in dry pyridine at 0° C. was added methanesulphonylchloride (3.5 equivalents) and the whole was stirred at room temperature for 3 hrs.

The solution was added to iced water and the solid filtered off. This was washed with water and digested in hot ethanol to give the title compound in 93% yield. M.p. 184°–186° C.

NMR: δd$_6$DMSO 11.75 (1H, d, NH), 8.05 (1H, s, H-6), 6.15 (1H, bt, H-1') 5.3 (1H, m, H-3'), 4.6–4.3 (3H, m, H-4', 8H-5'), 3.35 (6H, s, CH$_3$SO$_2$), 3.25 (1H, s, acetylenic H), 2.7–2.4 ppm (2H, m, H-2').

CHN Calc: C, 38.23; H, 3.92; N, 6.86%. Fnd: C, 38.29; H, 3.89; N, 6.78%.

In the following Examples 5–9 and 11–16 the title compounds were prepared by an analogous manner to that described in Example 2.

EXAMPLE 5

5'-O-Cyclopropanoyl-2'-deoxy-5-ethynyluridine

M.p.=320° C.

δCDCl$_3$ 8.2 (1H, bs, NH), 8.0 (1H, s, H-6) 6.25 (1H, t, H-1'), 4.6–4.1 (5H, m, H-3', H-5' and OH-3'), 3.17 (1H, s, acetylenic H), 2.52 (1H, m, H-2'), 2.21 (1H, m, H-2'), 1.7 (1H, m, cyclopropyl CH), 1.15–0.9 ppm (4H, m, cyclopropyl CH$_2$).

CHN Calc: C, 56.27; H, 4.99; N, 8.74%. Fnd: C, 56.18; H, 4.81; N, 8.35%.

EXAMPLE 6

2'-Deoxy-3',5'-di-O-cyclopropanoyl-5-ethynyluridine

M.p. 55° C.

NMR: δCDCl$_3$ 8.2 (1H, bs, NH), 7.97 (1H, s, H-6), 6.3 (1H, dd, H-1'), 5.26 (1H, m, H-3'), 4.4–4.25 (3H, m, H-4' and H-5') 3.18 (1H, s, acetylenic H), 2.6 (1H, m, H-2'), 2.2 (1H, m, H-2') 1.62 (2H, m, cyclopropyl CH), 1.15–0.8 ppm (8H, m, cyclopropyl CH$_2$).

CHN Calc: C, 58.78; H, 5.15; N, 7.21%. Fnd: C, 58.93; H, 4.98; N, 6.92%.

EXAMPLE 7

2'-Deoxy-5-ethynyl-5'-O-octanoyluridine

M.p. 141°–142° C.

NMR: δCDCl$_3$ 8.1 (1H, bs, NH), 7.93 (1H, s, H-6), 6.22 (1H, t, H-1'), 4.55–4.2 (3H, m, H-3' and H-5'), 4.15 (1H, m, H-4'), 3.19 (1H, s, acetylenic H), 2.6–2.35 (1H, m, H-2'), 2.3–2.0 (1H, m, H-2'), 1.7–1.15 (12H, m, octanoyl CH$_2$), 0.87 ppm (3H, octanoyl CH$_3$).

CHN Calc: C, 60.35; H, 6.87; N, 7.04%. Fnd: C, 60.40; H, 6.61; N, 7.20%.

EXAMPLE 8

5'-O-Benzoyl-2'-deoxy-5-ethynyluridine

M.p. 175°–176° C.

NMR: δ(d$_6$DMSO) 11.65 (1H, bs, NH), 8.3–7.3 (5H, m, aromatic Hs), 8.0 (1H, s, H-6), 6.13 (1H, t, H-1'), 5.45 (1H, bs, OH-3'), 4.8–4.25 (3H, m, H-3' and H-5'), 4.25–3.9 (2H, m, H-4' and acetylenic H), 2.4–2.1 ppm (2H, m, H-2').

CHN Calc: C, 60.67; H, 4.53; N, 7.86%. Fnd: C, 60.64; H, 4.45; N, 7.80%.

EXAMPLE 9

2'-Deoxy-3',5'-di-O-benzoyl-5-ethynyluridine

M.p. 192°–194° C.

NMR: δCDCl$_3$ 8.4 (1H, bs, NH), 8.15–7.4 (5H, m, aromatic Hs), 7.92 (1H, s, H-6), 6.38 (1H, dd, H-1'), 5.62 (1H, m, H-3'), 4.9–4.63 (2H, m, H-5'), 4.59 (1H, m, H-4'), 3.0 (1H, s, acetylenic H) 2.86–2.7 (1H, m, H-2'), 2.4–2.2 ppm (1H, m, H-2').

CHN Calc: C, 65.21; H, 4.38; N, 6.09%. Fnd: C, 65.33; H, 4.48; N, 5.95%.

EXAMPLE 10

5'-O-Benzoyl-2'-deoxy-5-ethynyl-3'-O-methanesulphonyluridine

To a stirred solution of 2'-deoxy-5'-benzoyl-5-ethynyluridine (1.58 g, 4.44 ml) in dry pyridine (15 ml at 0° C.) was added methanesulphonyl chloride (0.52 ml, 1.5 equivalents). This was left at 0° C. for 16 hours then poured onto ice/water. The pale yellow gum obtained was separated by decanting the aqueous supernatant layer, and taken up in dichloromethane. The solution was washed with water, dried (MgSO$_4$) and evaporated. The residue was triturated with ether to give the title compound.

1.35 g; 73%.

M.p. decomposed above 95° C.

NMR: δCDCl$_3$ 8.95 (1H, s, NH), 7.7 (1H, s, H-6), 7.65–7.1 (5H, dd, aromatic H's), 6.25 (1H, t, H-1'), 5.4 (1H, m, H-3'), 4.65 (3H, m, H-4' and H-5'), 3.1 (3H, s, CH$_3$), 3.05 (1H, s, acetylenic H), 2.35 ppm (2H, m, H-2').

CHN Calc: C, 54.54; H, 4.34; N, 6.70. Fnd: C, 54.19; H, 4.31; N, 6.61.

EXAMPLE 11

2'-Deoxy-5-ethynyl-5'-O-toluoyluridine

M.p. 180°–2° C.

NMR: δ(d$_6$DMSO) 11.65 (1H, s, NH), 7.95 (1H, s, H6), 7.9–7.25 (4H, dd, aromatic H's), 6.1 (1H, t, H-1'), 5.4 (1H, m, H-3'), 4.5 (2H, m, H-5'), 4.3 (1H, bs, OH), 4.1 (1H, m, H-4'), 4.0 (1H, s, acetylenic H), 2.35 (3H, s, CH$_3$), 2.2 ppm (2H, m, H-2').

CHN Calc: C, 61.62; H, 4.90; N, 7.57. Fnd: C, 61.48; H, 4.74; N, 7.42.

EXAMPLE 12

2'-Deoxy-3',5'-di-O-p-toluoyl-5-ethynyluridine

M.p. 200°–202° C.

NMR: δCDCl$_3$ 8.6 (1H, s, NH), 79 (1H, s, H-6), 8.0–7.1 (8H, H, aromatic H's) 6.35 (1H, t, H-1'), 5.1 (1H, m, H-3'), 4.7 (2H, m, H-5'), 4.5 (1H, m, H-4') 3.0 (1H, s, acetylenic H), 3.3–2.1 (2H, m, H-2'), 2.4 (3H, s, CH$_3$), 2.38 ppm (3H, s, CH$_3$).

CHN Calc: C, 66.38; H, 4.95; N, 5.74. Fnd: C, 66.22; H, 4.71; N, 5.64.

EXAMPLE 13

5'-O-p-Anisoyl-2'-Deoxy-5-ethynyluridine

M.p. 177°–179° C.

NMR: δ(d$_6$DMSO) 11.6 (1H, s, NH), 7.9 (1H, s, H-6), 8.0–7.0 (4H, dd, aromatic H's) 6.1 (1H, t, H-1'), 5.4 (1H, m, H-3'), 4.5 (2H, m, H-5'), 4.35 (1H, bs, 3'-OH), 4.1 (1H, m, H-4'), 4.05 (1H, s, acetylenic H), 3.7 (3H, s, OCH$_3$), 2.25 ppm (2H, m, H-2').

CHN Calc: C, 59.06; H, 4.70; N, 7.25. Fnd: C, 58.66; H, 4.55; N, 7.07.

EXAMPLE 14

2'-Deoxy-3',5'-di-O-p-anisoyl-5-ethynyluridine

M.p. 211°–213° C.

NMR: δ(d$_6$DMSO) 11.7 (1H, s, NH), 8.05 (1H, s, H-6), 8.0–6.95 (8H, m, aromatic H's), 6.2 (1H, t, H-1'), 5.55 (1H, m, H-3'), 4.5 (3H, m, H-4' and H-5'), 4.1 (1H, s, acetylenic H), 2.6 ppm (2H, m, H-2').

CHN Calc: C, 62.30; H, 4.65; N, 5.38. Fnd: C, 62.34; H, 4.48; N, 5.13.

EXAMPLE 15

3-Monosodium Salt of 2'-Deoxy-5-ethynyluridine

To an aqueous solution of 2'-deoxy-5-ethynyluridine (0.35 g, 1.4 mmoles) was added an aqueous solution of sodium hydroxide (0.55 g, 1.4 mmoles). The solution was freeze-dried twice and dried over P$_2$O$_5$ at 100° C. overnight in a drying pistol to yield the title compound as a hygroscopic, granular solid.

CHN for C$_{11}$H$_{11}$N$_2$NaO$_5$.0.22H$_2$O: Calc: C, 47.52; H, 4.0; N, 10.07; Na, 8.27%. Fnd: C, 47.16; H, 4.59; N, 9.94; Na, 8.33%.

EXAMPLE 16

| Tablet | |
|---|---|
| Compound of formula (I) | 100 mg |
| Lactose | 200 mg |
| Starch | 50 mg |
| Polyvinylpyrrolidone | 5 mg |
| Magnesium stearate | 4 mg |
| | 359 mg |

Tablets were prepared from the foregoing ingredients by wet granulation followed by compression.

EXAMPLE 17

| Ophthalmic Solution | |
|---|---|
| Active ingredient | 0.5 |
| Sodium chloride, analytical grade | 0.9 g |
| Thiomersal | 0.001 g |

-continued

| Ophthalmic Solution | |
|---|---|
| Purified water to | 100 ml |
| pH adjusted to | 7.5 |

EXAMPLE 18

Tablet Formulations

The following formulations A and B were prepared by wet granulation of the ingredients with a solution of povidone, followed by addition of magnesium stearate and compression.

| Formulation A | mg/tablet | mg/tablet |
|---|---|---|
| (a) Active ingredient | 250 | 250 |
| (b) Lactose B.P. | 210 | 26 |
| (c) Povidone B.P. | 15 | 9 |
| (d) Sodium Starch Glycollate | 20 | 12 |
| (e) Magnesium Stearate | 5 | 3 |
| | 500 | 300 |
| Formulation B | mg/tablet | mg/tablet |
| (a) Active ingredient | 250 | 250 |
| (b) Lactose | 150 | — |
| (c) Avicel PH 101 | 60 | 26 |
| (d) Povidone B.P. | 15 | 9 |
| (e) Sodium Starch Glycollate | 20 | 12 |
| (f) Magnesium Stearate | 5 | 3 |
| | 500 | 300 |
| Formulation C | mg/tablet | |
| Active ingredient | 100 | |
| Lactose | 200 | |
| Starch | 50 | |
| Povidone | 5 | |
| Magnesium stearate | 4 | |
| | 359 | |

The following formulations, D and E, were prepared by direct compression of the admixed ingredients. The lactose used in formulation E was of the direct compression type (Dairy Crest-"Zeparox").

| Formulation D | mg/capsule |
|---|---|
| Active Ingredient | 250 |
| Pregeletanised Starch NF15 | 150 |
| | 400 |
| Formulation E | mg/capsule |
| Active Ingredient | 250 |
| Lactose | 150 |
| Avicel | 100 |
| | 500 |

Formulation F (Controlled Release Formulation)

The formulation was prepared by wet granulation of the ingredients (below) with a solution of povidone followed by the addition of magnesium stearate and compression.

| | mg/tablet |
|---|---|
| (a) Active Ingredient | 500 |
| (b) Hydroxypropylmethylcellulose (Methocel K4M Premium) | 112 |
| (c) Lactose B.P. | 53 |
| (d) Povidone B.P.C. | 28 |
| (e) Magnesium Stearate | 7 |
| | 700 |

Drug release took place over a period of about 6–8 hours and was complete after 12 hours.

EXAMPLE 19

Capsule Formulations

Formulation A

A capsule formulation was prepared by admixing the ingredients of Formulation D in Example 20 above and filling into a two-part hard gelatin capsule. Formulation B (infra) was prepared in a similar manner.

| Formulation B | mg/capsule |
|---|---|
| (a) Active ingredient | 250 |
| (b) Lactose B.P. | 143 |
| (c) Sodium Starch Glycollate | 25 |
| (d) Magnesium Stearate | 2 |
| | 420 |
| Formulation C | mg/capsule |
| (a) Active ingredient | 250 |
| (b) Macrogol 4000 BP | 350 |
| | 600 |

Capsules were prepared by melting the Macrogol 4000 BP, dispersing the active ingredient in the melt and filling the melt into a two-part hard gelatin capsule.

| Formulation D | mg/capsule |
|---|---|
| Active ingredient | 250 |
| Lecithin | 100 |
| Arachis Oil | 100 |
| | 450 |

Capsules were prepared by dispersing the active ingredient in the lecithin and arachis oil and filling the dispersion into soft, elastic gelatin capsules.

Formulation E (Controlled Release Capsule)

The following controlled release capsule formulation was prepared by extruding ingredients a, b and c using an extruder, followed by spheronisation of the extrudate and drying. The dried pellets were then coated with release-controlling membrane (d) and filled into a two-piece, hard gelatin capsule.

| | mg/capsule |
|---|---|
| (a) Active Ingredient | 250 |
| (b) Microcrystalline Cellulose | 125 |
| (c) Lactose BP | 125 |
| (d) Ethyl Cellulose | 13 |
| | 513 |

EXAMPLE 20

Injectable Formulation

| | |
|---|---|
| Active ingredient | 0.200 g |
| Sterile, pyrogen free phosphate buffer (pH 9.0) to | 10 ml |

The active ingredient was dissolved in most of the phosphate buffer (35°–40° C.), then made up to volume and filtered through a sterile micropore filter into a sterile 10 ml amber glass vial (type 1) and sealed with sterile closures and overseals.

EXAMPLE 21

Intramuscular injection

| Active Ingredient | 0.20 g |
|---|---|
| Benzyl Alcohol | 0.10 g |
| Glycofurol 75 | 1.45 g |
| Water for Injection q.s. to | 3.00 ml |

The active ingredient was dissolved in the glycofurol. The benzyl alcohol was then added and dissolved, and water added to 3 ml. The mixture was then filtered through a sterile micropore filter and sealed in sterile 3 ml amber glass vials (type 1).

EXAMPLE 22

Syrup Suspension

| Active ingredient | 0.2500 g |
|---|---|
| Sorbitol Solution | 1.5000 g |
| Glycerol | 2.0000 g |
| Dispersible Cellulose | 0.0750 g |
| Sodium Benzoate | 0.0050 g |
| Flavour, Peach 17.42.3169 | 0.0125 ml |
| Purified Water q.s. to | 5.0000 ml |

The sodium benzoate was dissolved in a portion of the purified water and the sorbitol solution added. The active ingredient was added and dispersed. In the glycerol was dispersed the thickener (dispersible cellulose). The two dispersions were mixed and made up to the required volume with the purified water. Further thickening was achieved as required by extra shearing of the suspension.

EXAMPLE 23

Suppository

| | mg/suppository |
|---|---|
| Active Ingredient (63 μm)* | 250 |
| Hard Fat, BP (Witepsol H15 - Dynamit NoBel) | 1770 |
| | 2020 |

*The active ingredient was used as a powder wherein at least 90% of the particles were of 63 μm diameter or less.

One-fifth of the Witepsol H15 was melted in a steam-jacketed pan at 45° C. maximum. The active ingredient was sifted through a 200 μm sieve and added to the molten base with mixing, using a silverson fitted with a cutting head, until a smooth dispersion was achieved. Maintaining the mixture at 45° C., the remaining Witepsol H15 was added to the suspension and stired to ensure a homogenous mix. The entire suspension was passed through a 250 μm stainless steel screen and, with continuous stirring, was allowed to cool to 40° C. At a temperature of 38° C. to 40° C. 2.02 g of the mixture was filled into suitable plastic moulds. The suppositories were allowed to cool to room temperature.

EXAMPLE 24

Pessaries

| | mg/pessary |
|---|---|
| Active ingredient 63 μm | 250 |
| Anhydrate Dextrose | 380 |
| Potato Starch | 363 |
| Magnesium Stearate | 7 |
| | 1000 |

The above ingredients were mixed directly and pessaries prepared by direct compression of the resulting mixture.

EXAMPLE 25

Antiviral and Toxicity Testing

Human cytomegalovirus (HCMV) was assayed in monolayers of either MRC5 cells (human embryonic lung) or Detroit 532 cells (human foreskin fibroblasts) in multiwell trays. Activity of compounds was determined in the plaque reduction assay, in which a cell monolayer was infected with a suspension of HCMV, and then overlaid with nutrient agarose in the form of a gel to ensure that there was no spread of virus throughout the culture. A range of concentrations of compound of known molarity was incorporated in the nutrient agarose overlay. Plaque numbers at each concentration were expressed as percentages of the control and a dose-response curve was drawn. From this curve the 50% inhibitory concentration ($IC_{50}$) was estimated.

Varicella zoster virus (VZV) was assayed in MRC5 cells by a similar method to that for HCMV with the omission of the agarose overlay.

Herpes simplex type 1 (HSV1) was assayed in Vero cells in a similar method to that described for the HCMV assay.

Cell toxicity was assessed in a cell growth inhibition assay. Subconfluent cultures of Vero cells grown on 96-well microtiter dishes were exposed to different dilutions of drug, and cell viability determined daily on replicate cultures using uptake of a tetrazolium dye (MTT). The concentration required for a 50% inhibition of cell viability at 96 hours is termed $CCID_{50}$.

Results are shown in Table 1.

TABLE 1

| Compound | | $IC_{50}(\mu M)$ | | | $CCID_{50}(\mu M)$ |
|---|---|---|---|---|---|
| 3'0 | 5'0 | HSV1 | VZV | HCMV | at 96 hr. |
| H | H | 4.5 | 0.06–0.3 | 0.05–0.03 | 0.3–3.0 |
| H | Cyclopropanoyl | >20.0 | 6.5 | 0.9 | 15.0 |
| cyclopropanoyl | Cyclopropanoyl | >20.0 | 24.0 | 2.0 | >100.0 |
| H | Benzoyl | >20.0 | 0.7 | 0.3 | 1.3 |
| Benzoyl | Benzoyl | >20.0 | >20.0 | 4.7 | >100.0 |
| H | p-Anisoyl | >20.0 | >20.0 | 2.8–3.7 | 3.0 |
| p-Anisoyl | p-Anisoyl | >20.0 | >20.0 | 20.7 | >100.0 |
| H | p-Toluoyl | >20.0 | >20.0 | 3.4 | 0.8 |
| p-Toluoyl | p-Toluoyl | >20.0 | >20.0 | | >100.0 |
| H | Pivaloyl | >20.0 | 0.6 | 0.4 | 10.2 |
| Pivaloyl | Pivaloyl | >20.0 | 5.5 | 2.0 | >100.0 |
| Methanesulphonyl | Methanesulphonyl | >20.0 | 16.0 | >50.0 | |
| Acetyl | Acetyl | >20.0 | 12.5 | 2.0–6.0 | 42.0 |
| H | m-Cl Benzoyl | | <0.2 | 0.46 | 19.0 |
| m-Cl Benzoyl | m-Cl Benzoyl | | 1.1 | 2.7 | >100.0 |
| H | Octanoyl | | <0.2 | 2.2 | 1.8 |
| H | p-Tosyl | | | 5.6 | |
| Acetyl | Acetyl | >20.0 | 0.3 | 7.3 | >100.0 |

We claim:

1. A method of treating a VZV infection in a human having a VZV infection comprising the administration to said human of an effective VZV infection treatment amount of 2'-Deoxy-5-ethynyl-3',5'-di-O-pivaloyl uridine or a pharmaceutically acceptable salt thereof.

2. A method of treating a VZV infection in a human having a VZV infection comprising the administration to said human of an effective VZV infection treatment amount of 2'-Deoxy-3',5'-di-O-acetyl-5-ethynyluridine or a pharmaceutically acceptable salt thereof.

3. A method of treating a VZV infection in a human having a VZV infection comprising the administration to said human of an effective VZV infection treatment amount of 2'-Deoxy-3',5'-di-O-cyclopropanoyl-5-ethynyluridine or a pharmaceutically acceptable salt thereof.

4. A method of treating a VZV infection in a human having a VZV infection comprising the administration to said human of an effective VZV infection treatment amount of 2'-Deoxy-3',5'-di-O-benzoyl-5-ethynyluridine or a pharmaceutically acceptable salt thereof.

5. A method of treating a CMV infection in a human having a CMV infection comprising the administration to said human of an effective CMV infection treatment amount of 2'-Deoxy-5-ethynyl-3',5'-di-O-pivaloyl uridine or a pharmaceutically acceptable salt thereof.

6. A method of treating a CMV infection in a human having a CMV infection comprising the administration to said human of an effective CMV infection treatment amount of 2'-Deoxy-3',5'-di-O-acetyl-5-ethynyluridine or a pharmaceutically acceptable salt thereof.

7. A method of treating a CMV infection in a human having a CMV infection comprising the administration to said human of an effective CMV infection treatment amount of 2'-Deoxy-3',5'-di-O-cyclopropanoyl-5-ethynyluridine or a pharmaceutically acceptable salt thereof.

8. A method of treating a CMV infection in a human having a CMV infection comprising the administration to said human of an effective CMV infection treatment amount of 2'-Deoxy-3',5'-di-O-benzoyl-5-ethynyluridine or a pharmaceutically acceptable salt thereof.

* * * * *